US009383292B1

(12) United States Patent
Kornev et al.

(10) Patent No.: US 9,383,292 B1
(45) Date of Patent: Jul. 5, 2016

(54) FLEXIBLE FIBER-BASED MICRO AND NANOFLUIDICS FOR PROBING LIQUIDS

(75) Inventors: Konstantin G. Kornev, Clemson, SC (US); Chen-Chih Tsai, New Taipei (TW); David Lukas, Rochlice (CZ); Petr Mikes, Liberce (CZ)

(73) Assignee: CLEMSON UNIVERSITY, Clemson, SC (US)

(*) Notice: Subject to any disclaimer, the term of this patent is extended or adjusted under 35 U.S.C. 154(b) by 713 days.

(21) Appl. No.: 13/611,971

(22) Filed: Sep. 12, 2012

Related U.S. Application Data

(60) Provisional application No. 61/534,029, filed on Sep. 13, 2011.

(51) Int. Cl.
*D04H 1/74* (2006.01)
*G01N 1/10* (2006.01)
*B32B 5/32* (2006.01)

(52) U.S. Cl.
CPC ............ *G01N 1/10* (2013.01); *B01D 2239/025* (2013.01); *B32B 5/32* (2013.01)

(58) Field of Classification Search
CPC ... G01N 27/127; G01N 27/126; G01N 15/14; G01N 2291/02863; D01D 5/0038; D01D 5/0007; D01D 5/0069; D01D 5/003; D01D 5/0084; D01D 5/247; D01D 5/0023; D01D 5/24; D01D 10/00; D01D 5/0046; D01D 1/04; A61L 2400/12; A61L 27/26; A61L 31/10; A61L 27/34; A61L 27/48
See application file for complete search history.

(56) References Cited

U.S. PATENT DOCUMENTS

2008/0265469 A1\* 10/2008 Li et al. .................. 264/433
2011/0194304 A1 8/2011 Han et al.

OTHER PUBLICATIONS

Ali et al. "Direct electrospinning of highly twisted, continuous nanofiber yarns", The Journal of the Textile Institute, Jan. 2012, v. 103, No. 1, pp. 80-88, published on-line Apr. 2011.\*
Chung et al. "Control of Nanoparticles on Nanofiber via Magnetic Electrospinning", NSTI-Nanotech 2009, 2009, v. 1, pp. 180-182.\*
D. Monaenkova, M.S. Lehnert, T. Andrukh, C. E. Beard, B. Rubin, A. Tokarev, W.-K, Lee, P. H. Adler and K. G. Kornev, Butterfly proboscis: combining a drinking straw with a nanosponge facilitated diversification of feeding habits, *J. R. Soc. Interface*, 2011, DOI: 10.1098/rsif.2011.0392.
D. H. Reneker, A. L. Yarin, E. Zussman and H. Xu, *Adv. Appl. Mech.*, 2007,41, 43-195.
D. H. Reneker and A. L. Yarin, *Polymer*, 2008, 49, 2387-2425.
Y. Dzenis, *Science*, 2008,319,419-420.
G. C. Rutledge and S. V. Fridrikh, *Adv. Drug Delivery Rev.*, 2007,59, 1384-1391.

(Continued)

*Primary Examiner* — Yelena G Gakh
(74) *Attorney, Agent, or Firm* — Dority & Manning, P.A.

(57) ABSTRACT

A fluidic probe comprising a plurality of oriented fibers with individual fibers having nano-pores in the fiber bodies, the oriented fibers being twisted together, wherein the twisted oriented fibers form micro-pores between the individual fibers, is disclosed. The fluidic probe exhibits excellent flexibility, deployability and absorptive capacity. The enhanced absorptive capacity is due to the fluid absorption via capillary action of the nano-pores and fluid transport via the micro-pores. The probes can also be formed so as to be remotely controlled by electromagnetic fields and thus be used in a hands-free fashion. With these probes, the paradigm of a stationary microfluidic platform can be shifted to include flexible structures that can include multiple microfluidic sensors in a single fibrous probe.

10 Claims, 5 Drawing Sheets

(56) References Cited

OTHER PUBLICATIONS

J. Fang, H. T. Niu, T. Lin and X. G. Wang, *Chin. Sci. Bull.*, 2008, 53, 2265-2286.

E. M. Janle and J. E. Sojka, *Contemporail Top. Lab. Animal Sci.*, 2000, 39, 47-50.

C. M. Huang, C. C. Wang, M. Kawai, S. Barnes and C. A. Elmets, *J. Chromatogr., A*, 2006, 1109, 144-151.

V. Reukov, A Vertegel, O. Burtovyy, K. G. Kornev and I. Luzinov, *Mater. Sci. Eng. C*, 2009, 29, 669-673.

D. Monaenkova and K. G. Kornev, *J. Colloid Inteljace Sci.*, 2010, 348, 240-249.

G. Callegari, I. Tyomkin, K. G. Kornev, A. V. Neimark and Y. L. Hsieh, *J. Colloid InteJface Sci.*, 2011, 353, 290-293.

K. G. Kornev, X. Ren and Y. Dzenis, *Journal of Engineered Fibers and Fabrics*, 2009, 4, 14-23.

A. M. Afifi, S. Nakano, H. Yamane and Y. Kimura, *Macromol. Mater. Eng.*, 2010, 295, 660-665.

K. Zhang, X. F. Wang, Y. Yang, L. L. Wang, M. F. Zhu, B.S. Hsiao and B. Chu, *J. Polym. Sci., Part B: Polym, Phys.*, 2010, 48, 1118-1125.

F. Dabirian and S. A. H. Ravandi, Fibl .es *Text. Eastern Eur.*, 2009, 17, 45-47.

M. B. Bazbouz and G. K. Stylios, *Ew'•Polym. J.*, 2008, 44, 1-12.

A. Mondal, R. Borah, A. Mukherjee, S. Basu, M. Jassal and A. K. Agrawal, *J. Appl. Polym. Sci.*, 2008, 110, 603-607.

F. L. Zhou and R. H. Gong, *Polym. Int.*, 2008, 57, 837-845.

S. Moon and R. J. Farris, *Polym. Eng. Sci.*, 2007, 47, 1530-1535.

E. Smit, U. Buttner and R. D. Sanderson, *Polymer*, 2005, 46, 2419-2423.

W. E. Teo and S. Ramakrishna, *Nanotechnology*, 2006, 17, R89-RI06.

\* cited by examiner

FLEXIBLE FIBER-BASED MICRO AND NANOFLUIDICS FOR PROBING LIQUIDS

CROSS REFERENCE TO RELATED APPLICATION

The present application claims filing benefit of U.S. Provisional Patent Application Ser. No. 61/534,029 having a filing date of Sep. 13, 2011, which is incorporated herein in its entirety by reference.

STATEMENT REGARDING FEDERALLY SPONSORED RESEARCH OR DEVELOPMENT

This invention was made with government support under Grant Nos. CMMI-0826067 and CMMI-0825773, EFRI 0937985 awarded by the National Science Foundation and under Contract No. FA8650-09-D-5900 awarded by the U.S. Air Force. The government has certain rights in the invention.

BACKGROUND

Many butterflies, moths, and other insects easily probe and identify potable liquids with their proboscises. The butterfly proboscis has a two-level pore hierarchy as illustrated in FIG. 1. The proboscis is nanoporous in its lateral dimension, which comprise the first level of pore hierarchy. These nanopores are created by overlapping legulae. The legulae are formed like a fence on two tubular musculature structures known as galeas. In FIG. 1 is visible the central groove with the legulae (shown by the arrow) looking like a fence at the dorsal side of the proboscis. The liquid wicks into the food canal through the nanopores formed by two nearest legulae. Galea tubes have lateral semi-cylindrical indentations, so that when galeas are locked by legulae, these two indentations form the food canal. The food canal, whose diameter ranges from a few to tens of micrometers, forms the second level of pore hierarchy. Thus, the proboscis can be considered as a drinking straw with a nanosponge.

The ability to manipulate the proboscis, which can be coiled and uncoiled like a party noisemaker, is closely linked to its remarkable fluid transport capabilities. In addition, the proboscis can be flawlessly positioned in a targeted liquid drop. Insect proboscises feature integrated sensors and filters that distinguish foods and multiple different chemicals. Integrating all of these features—ability to deploy, sense and sample, and identify low-volume fluids—into a single micro-nanofluidic device is attractive and promising for many engineering applications.

The basic concept of electrostatic spinning (or electrospinning) a polymer to form extremely small diameter fibers was first patented in the early twentieth century. Electrostatically spun fibers and nonwoven webs formed therefrom exhibit very high surface areas and can be formed from a wide variety of polymers and composites. These materials have traditionally found use in filtration applications, but have begun to gain attention in other industries, including in nonwoven textile applications as barrier fabrics, wipes, medical and pharmaceutical uses, and the like.

What is needed in the art is an artificial, biomimetic probe that possesses many properties of the natural proboscis. In addition, what is needed is an industrially scalable method of formation that can provide reproducible wetting, wicking, and mechanical characteristics for the probes thus produced. Precision control of these properties as is found in the natural proboscis would be of great benefit.

SUMMARY

According to one embodiment, disclosed is a fluidic probe. The probe includes a plurality of oriented fibers that include nano-sized pores. The plurality of oriented fibers can be twisted together to form the fluidic probe such that the fibers include micro-sized pores between individual fibers of the fluidic probe.

Also disclosed is a method of forming a fluidic probe. For instance, a method can include electrospinning a solution or melt comprising a polymer to form a plurality of fibers that include nano-sized pores. The method can also include gathering the plurality of fibers to form a fiber bundle and twisting the fiber bundle to form the fluidic probe. Following the twisting of the fiber bundle, there can exist micro-sized pores between individual fibers of the fluidic probe.

A method for analyzing a fluid is also described. A method can include manipulating a fluidic probe to contact a liquid with an end of the fluidic probe, wherein upon contact of the fluid with the end of the fluidic probe, at least a portion of the liquid is absorbed by the fluidic probe.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

DETAILED DESCRIPTION

Figure 1:
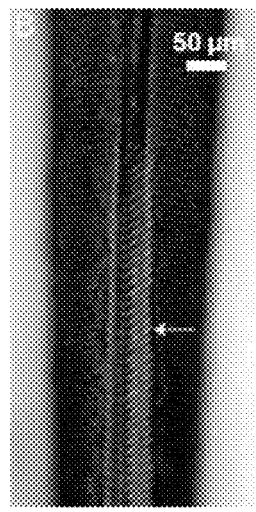
FIG. 1 is a magnified image of a butterfly proboscis.

Reference will now be made in detail to various embodiments of the disclosed subject matter, one or more examples of which are set forth below. Each embodiment is provided by way of explanation of the subject matter, not limitation of the subject matter. In fact, it will be apparent to those skilled in the art that modifications and variations may be made in the present disclosure without departing from the scope or spirit of the subject matter. For instance, features illustrated or described as part of one embodiment, may be used in another embodiment to yield a still further embodiment. Thus, it is intended that the present disclosure cover such modifications and variations as come within the scope of the appended claims and their equivalents.

The present disclosure is generally directed to a method of fabrication of porous flexible probes which can function as artificial proboscises. The probes can possess two levels of pore hierarchy: nano-sized pores that can enhance the capillary action of the probes and micro-sized pores that can speed up fluid transport through the probes. In one embodiment, the probes can also be formed so as to be remotely controlled by electromagnetic fields. Accordingly, the probes can be used in such an embodiment in a hands-free fashion. For instance, using a probe, one can approach a drop of hazardous liquid or a biofluid (e.g., blood, mucus, etc.), absorb it, and safely deliver it to an analytical device all in a hands-free fashion. With these probes, the paradigm of a stationary microfluidic platform can be shifted to include flexible structures that in one embodiment can also allow one to pack multiple microfluidic sensors into a single fibrous probe.

The natural structural organization of the butterfly proboscis is the guide that has been used to design a probe that simultaneously has a strong driving suction pressure and a fast wicking rate. The probe material includes a two-level pore hierarchy that includes nano-sized pores that provide strong capillary action and micro-sized pores that provide rapid wicking. In general, nano-sized pores can have an average cross-sectional diameter of less than about 200 nanometers (nm), while micro-sized pores can have an average cross-sectional diameter of less than about 10 micrometers ($\mu m$), for instance from about 1 $\mu m$ to about 10 $\mu m$. In one embodiment, the nano-sized and/or micro-sized pores can have an aspect ratio greater than 1. Thus, the pores can have a length greater than the cross-sectional width. For instance, micro-sized pores of a probe can extend along a length of the probe that can encompass a portion of or the entire length of the probe.

Materials and design strategies utilized for making the probes can provide excellent flexibility, deployability, and absorptive capacity, using electrospun fibers as building blocks for the micro- and nanofluidic probes. In forming the disclosed probes, the electrospun fibers can be made so as to include nanoporosity (i.e., nano-sized pores) in the individual fibers. In addition, a plurality of the porous fibers can be bundled and twisted into a yarn such that microporosity (i.e., micro-sized pores) are formed between individual fibers of the yarn. The yarns thus formed can constitute a broad class of flexible, lightweight probes that can be utilized in many applications dealing with liquid handling and manipulation.

Figure 2:
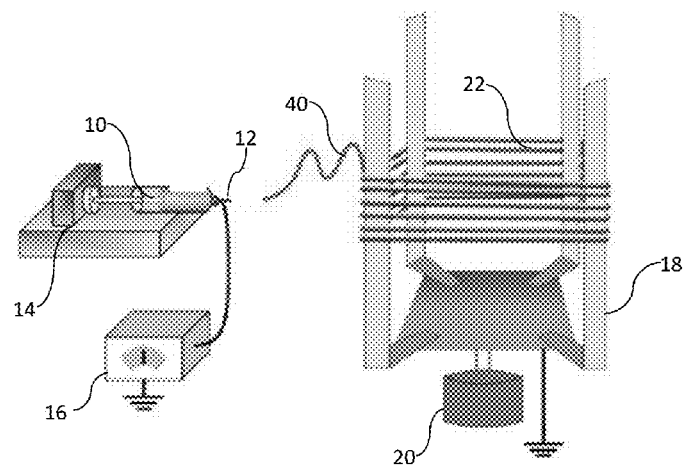
FIG. 2 illustrates one embodiment of an electrostatic spinning system as may be utilized in forming probes as described herein.

Electrospinning is a relatively simple and inexpensive technique as may be utilized for the fabrication of the individual fibers of the probes. According to the electrospinning process, a polymer solution (e.g., generally a solution of less than about 20 wt. % polymer, for instance from about 2 wt. % to about 18 wt. % polymer) to be spun is charged to a high voltage that is typically measured in kilovolts. FIG. 2 schematically illustrates one system as may be used for forming a probe. The system includes a syringe 10 filled with polymer melt or solution, a metal needle 12, a syringe pump 14, a high-voltage power supply 16, a rotating collector 18, and a motor 20. The basic electrospinning process utilizes the high voltage power supply 16 to apply an electrical field to the polymer melt or solution held in the metal needle 12, inducing a charge on the individual polymer molecules. Upon application of the electric field, a charge and/or dipolar orientation will be induced at the air-surface interface 60. The induction causes a force that opposes the surface tension. At critical field strength, when the charge is sufficient to overcome the surface tension of the melt or solution, the surface of the polymer solution or melt undergoes a sudden transformation from flat to cusped, followed by emanation of a jet 40. On its way to the oppositely charged, grounded collector 18, the jet 40 is elongated and accelerated by the external electric field such that the jet 40 bends and twists causing the polymer to stretch. Simultaneously, the solvent evaporates, leaving behind a polymeric fiber 22 on the collector.

In general, any polymer capable of being electrospun can be utilized in forming the probes. For instance, high performance polymers such as polyaramids (e.g., liquid crystal polymers) and polyamides (e.g., nylon), textile fibers such as polyesters (e.g., polyethylene terephthalate), or biopolymers (e.g., polysaccharides) can be utilized. In one embodiment, an electroactive polymer can be utilized in forming the probes. Polymers as may be utilized in forming the probes can include, without limitation, poly(ethylene oxide), cellulose acetate, poly(methyl methacrylate), polyacrylonitrile, polyvinyl alcohol, polyvinylidene fluoride, and so forth as well as blends of one or more polymers. By way of example, a polymer that possesses piezoelectric properties including, without limitation, polypropylene, polystyrene, poly(methyl methacrylate), semi-crystalline polyamides such as odd numbered nylons, amorphous polymers such as vinyl acetate, as well as combinations of polymers can be utilized in forming individual fibers of the probes. Moreover, a probe can include fibers that differ from one another and each fiber of a probe can be formed of one or more different materials. For instance, the fibers can be formed of a blend of multiple polymers.

According to one embodiment, the probe can include polyvinylidene fluoride (PVDF) electrospun fibers. In the past, PVDF has been considered one of the most difficult polymers to electrospin because it must be heated during the electrospinning process. However, PVDF is attractive for use in forming the probes as it exhibits high chemical inertness and thermal stability due to the presence of the —$CF_2$— groups. Another advantageous PVDF property is that the $C_2H_2F_2$ molecular units of the polymer chains possess large dipole moments. These dipoles point from the electronegative fluorine to the electropositive hydrogen. Under certain solidification conditions as described further herein, the dipoles can form ordered structures that can cause the formed fibers to be ferroelectric. In this embodiment, the produced probes can be manipulated with electromagnetic fields to grab and absorb distant droplets of liquids. This can be particular beneficial when considering hands-free applications for the probes, for instance in the manipulation of potentially hazardous liquids.

To form nano-sized pores in the fibers, a polymeric blend can be electrospun that includes one or more polymers that will form the final fiber in conjunction with a sacrificial polymer that can be removed either during or following the electrospinning process to form the nano-sized pores in the final fiber. By way of example, a water-soluble polymer such as poly(ethylene oxide) (PEO) can be utilized as the sacrificial polymer. Of course, other water soluble polymers can be utilized as the sacrificial polymer such as, without limitation, cellulose-based polymers (e.g., hydroxyethylcellulose, ethylcellulose, cellulose ethers, etc.), polyvinyl alcohol, partially esterified polyacrylic acid, and so forth. Moreover, the sacrificial polymer need not be water soluble and the solvent for use in removing the sacrificial polymer need not be water. Any solvent can be utilized that is capable of dissolving the sacrificial polymer without likewise dissolving the polymer that forms the final fiber so as to form the nano-sized pores in the electrospun fibers.

A water soluble sacrificial polymer may be preferred in one embodiment, as this can simplify removal of the sacrificial polymer. For instance, in one embodiment the electrospinning process can be carried out at a high relative ambient humidity, for example from about 55% to about 65% ambient relative humidity, and the nano-sized pores can be formed in the electrospun fibers during the fiber spinning process utilizing a water soluble sacrificial polymer. In this embodiment, a separate process step for removal of the sacrificial polymer following the electrospinning process (e.g., soaking the formed fibers in a solution of the solvent) is not necessary.

The porosity of the electrospun fiber can depend upon the relative amounts of the polymers used in the forming process. For instance, the electrospun fibers can have a porosity of from about 50% to about 85% or from about 75% to about 82%. The porosity of the electrospun fibers is not limited to such ranges, however, and fibers with higher or lower porosities are also encompassed herein.

The electrospun fibers can include additional materials in conjunction with the formation polymers. For instance, in one embodiment, the electrospun fibers can be formed so as to include nano-sized particles in the fibers. The particles can either be included in the solution that is electrospun to form the fibers or can be embedded in the fibers following formation, for instance via absorption or adsorption of the particles in/on the electrospun fibers. In one embodiment, fibers can include superparamagnetic nanoparticles (e.g., FERRO nano-sized particles available from CMS Magnetics), thus making the probes reactive to a magnetic field. Magnetically actuated probes are attractive candidates for probing aqueous solutions, blood or any biofluids that do not interfere with the magnetic field.

The probes can be used as sensors in one embodiment. For instance, one or more sensing devices can be included in the fibers of a probe. By way of example, the sensing device can be a material that can exhibit an optically detectable response in the presence of a particular compound. The response of the sensing device can provide information with regard to the presence or amount of the compound in a liquid to be examined by the probe. For example, the sensing device can be a fluorescent dye that emits a distinct spectrum when in the presence of a specific compound. In another embodiment, the sensing device can be a light absorber, and the optically detectable quenching effect of the sensing device can indicate information with regard to the presence or amount of the targeted compound. According to one embodiment, the sensing device can be a pH indicator that can be a material for which the emission spectrum can vary depending upon the pH of the local environment. pH indicators as may be utilized as a sensing device in a fiber can include, without limitation, coumarin-based pH sensitive dyes, phthalein type dyes, fluorescein type dyes, rhodamine type dyes, and so forth. Of course, other sensing devices as are generally known in the art may be utilized in conjunction with the probes, and the sensing devices are in no way limited to pH sensors.

In one embodiment, multiple probes, each including the same or different sensing devices, can be utilized in conjunction with one another, which can be utilized to form a probing device in the form of an artificial 'octopus' with many different arms, each a different probe as described herein, simultaneously probing and analyzing a liquid in different locations for one or multiple targeted compounds.

While the overall dimensions of the nanofibers can vary depending upon materials, fiber formation parameters, and so forth, the electrospun fibers can generally have an average diameter of less than about 2 for instance between about 0.5 μm and about 2 μm. For example, the average fiber diameter can be less than about 1.5 μm, or about 1.2 μm. The individual fibers can be pliable, for instance the individual fibers can have a modulus of elasticity of less than about 3 megapascals (MPa), or less than about 2 MPa. For instance, the individual fibers can have a modulus of elasticity of between about 1 MPa and about 2 MPa, or about 1.5 MPa.

When the dimensions of the only pores in a material are in the nanometer range, the rate of wicking becomes very slow. Therefore, in order to speed up fluid transport in the disclosed probes, integration of the nanoporous fibers into yarns has been carried out to provide an additional degree of freedom in the probe design. Yarns may thus have two types of pores: nanometer-sized pores in the fiber themselves and micrometer-sized pores between the fibers of the yarn. Therewith, the absorption kinetics can be improved as compared to the kinetics observed in materials having a unimodal pore size distribution.

Figure 3:
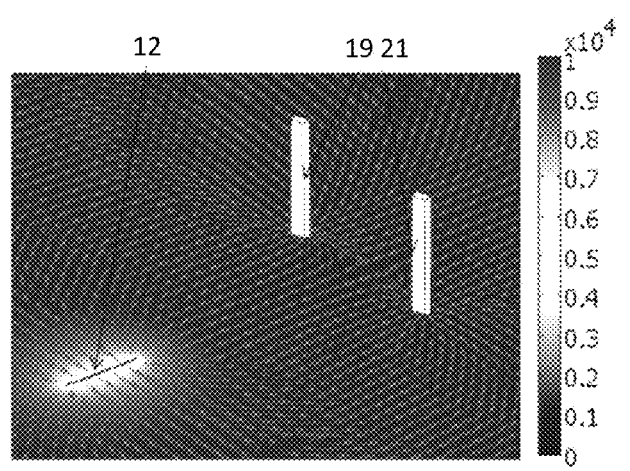
FIG. 3 schematically illustrates a perspective view of the electric field of the system of FIG. 2 during operation.

One benefit of an electrospinning system as is illustrated in FIG. 2 is the ability of the formation process to form an array of oriented fibers, i.e., the fibers are generally aligned with one another on the collection device. Moreover, not only can the device collect the nanofibers in an oriented array, it can also be utilized to twist the fibers into a yarn. The formation method of FIG. 2 takes advantage of methods of formation of ordered fiber arrays in which fiber orientation can be significantly increased when the target electrode 18 is formed of unipolar parallel plates. Near the plates, the electric field is almost two-dimensional, as demonstrated in FIG. 3, which provides a perspective view of the electric field in the region between the needle 12 and two arms 19, 21 of the collector 18. The arrows denote the direction of the electrostatic field, and different shades in the plane correspond to different potentials as specified in the vertical bar adjacent the figure. Since both plates 19, 21 are kept at the same voltage, the electric field lines branch out from a singular line, which divides the interplate gap in halves. Near the two charged plates, the electric field vector E has opposite directions. Therefore, if two identical charges q are situated in different halves of the interplate gap, they will be pushed by the force F=qE toward different plates. For the polymer jet, this specific electrode geometry works as a natural stretching device. As a charged jet approaches the electrodes and is about to land in between, the electric force pulls the jet in different directions. Because the fibers are charged, they repel each other. As a result, the fibers align perpendicular to the plates. To collect more fibers, it is convenient to use a mandrel with four or more metal arms, such as the collector 18 of FIG. 2. Each pair of aluminum bars collects a band of oriented nanofibers.

After formation of the array including the oriented electrospun fibers, the fibers can be collected from the mandrel and a yarn can be formed. The formed yarn can function as a probe as described herein. FIGS. 4A-4E illustrate steps in a probe formation process. As can be seen in FIG. 4A, the electrospun fibers 22 can form an ordered array between two plates 19, 21 of a collector. The fibers can be removed from the collector as shown in FIG. 4B. In this embodiment, the device for fiber collection can include two circular wire brushes 24, 25 mounted co-axially and attached to two miniature DC motors. The two arms 19, 21 of the collector 18 support the rolled brushes 24, 25, as shown in FIG. 4B. The nanofibers are gathered as a fibrous cylindrical shell attached from its ends to the brushes (FIG. 4C). The same device can then be used to form a yarn by spinning the brushes in opposite directions: the brushes twist the fibrous shell to a predetermined density, thus forming a yarn. The yarn twisting device allows control of the yarn diameter and density by changing the total number of revolutions of the supporting brushes. By way of example and without limitation, the yarn can be formed by applying a number of twists per centimeter of from about 2 to about 20, for instance from about 5 to about 18 twists per centimeter, or from about 10 to about 15 twists per centimeter.

Figure 4:
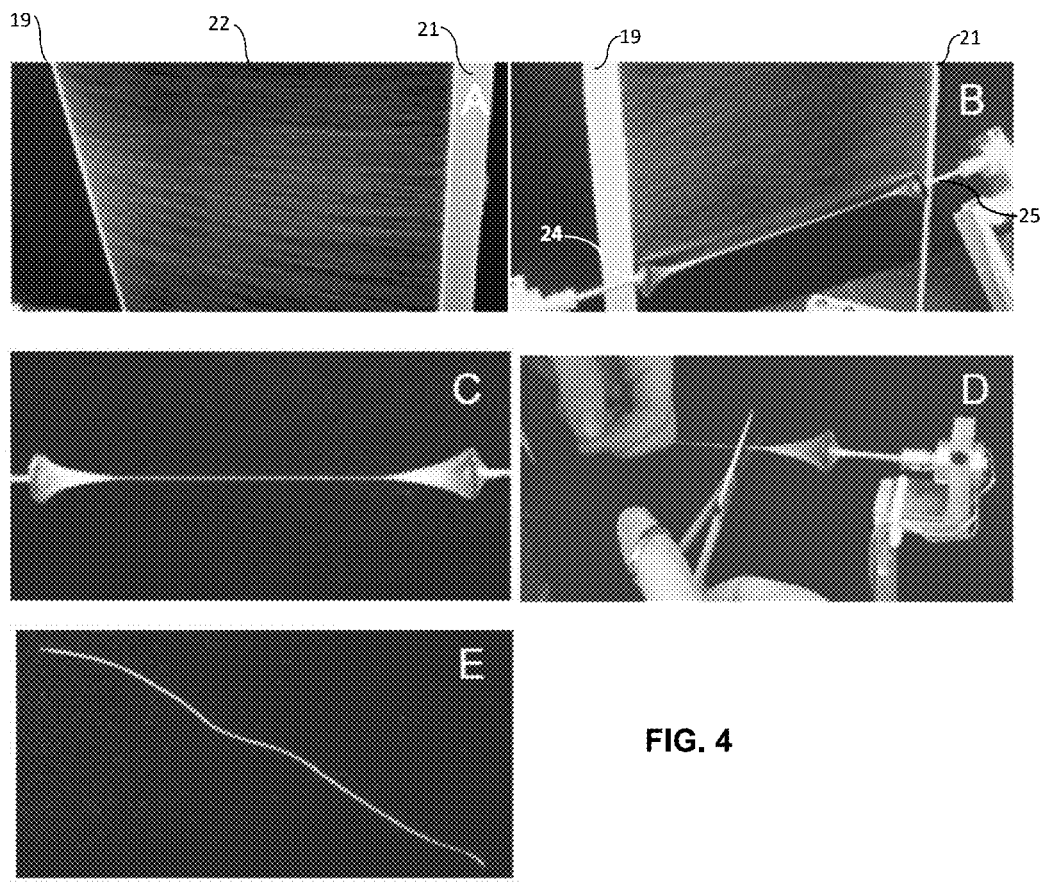
FIG. 4 illustrates steps in a probe formation process including formation of an ordered array of electrospun fibers (FIG. 4A), gathering of the fibers of the array (FIG. 4B), twisting of the gathered fibers to form a yarn (FIG. 4C), removal of the yarn from the device (FIG. 4D), and the finished probe (FIG. 4E).
Figure 5:
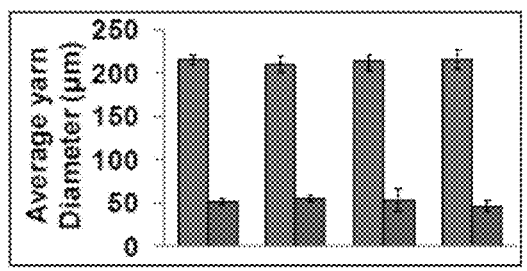
FIG. 5 graphically illustrates the diameter of several yarns formed of electrospun fibers as described herein.

After twisting, the yarn can be cut into pieces (FIG. 4D) to form the fiber-based probe (FIG. 4E). While the overall dimensions of the formed probe can vary, for instance depending upon the total number of electrospun fibers incorporated in a probe, in general, a probe can be from about 10 µm to about 500 µm, from about 20 µm to about 400 µm, from about 40 µm to about 300 µm, or from about 50 µm to about 150 µm in average diameter, and can exhibit both nanoporosity in the individual fibers and micro porosity between fibers of the yarn. For example, following a 15 minute electrospinning collection time for the electrospun fibers on the collector and with the distance between the two arms 19, 21 at 20 cm, the supporting brushes can apply about 120 twists to form a yarn (i.e., 6 twists per centimeter in this example), and the final probe can have a diameter of about 50 µm, as shown in FIG. 5. In comparison, following a one hour collection time for electrospun fibers on the same collector, the supporting brushes can apply about 100 twists to form a probe having a diameter of about 210 µm, as shown in FIG. 5. Accordingly, through variations in the formation process such as collection time, distance between the collecting arms, and number of twists applied to the collected fibers, a probe of varying dimensions and density can be formed. The permeability of the yarns can also vary depending upon the number of twists per centimeter, the overall dimensions of the yarn, etc. For example, the yarn can have a permeability of from about $10^{-15}$ m$^2$ to about $10^{-10}$ m$^2$, or from about $5 \times 10^{-14}$ m$^2$ to about $10^{-12}$ m$^2$.

The probes can be flexible. For example, a probe can exhibit a Young's modulus of from about 10 MPa to about 500 MPa, from about 20 MPa to about 300 MPa, or from about 50 MPa to about 220 MPa, in one embodiment.

The probes can be utilized for absorption of small amounts of fluids in a large variety of applications. For instance, the probes can be utilized as active elements in nanofluidic devices, chemical and biomedical sensors, forensic probes, and in many other fields where probing small amounts of liquids can be utilized in material processing and analysis For hands-free deployment and positioning of a probe, a probe can be formed so as to exhibit ferroelectric and/or piezoelectric characteristics, for instance as a result of the polymers utilized in the electrospinning process or by virtue of additional materials included in the electrospun fibers. In this embodiment, a probe can be flexed and controlled by applying an electromagnetic field. For instance, a probe can be used for grabbing and probing hazardous liquids or biofluids in a hands-free fashion.

Figure 6:
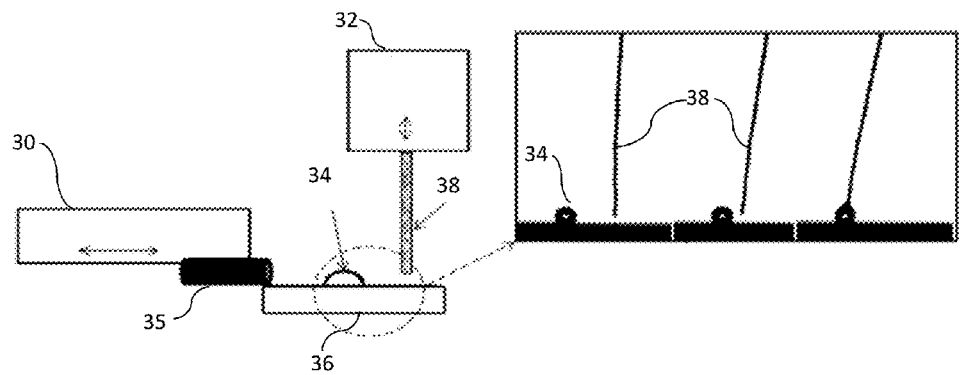
FIG. 6 illustrates a method of utilizing a probe that is reactive to a magnetic field.

An example of a method for utilization of a probe that is reactive to a magnetic field is shown in FIG. 6. A system can include a positioning stage 30 associated with a magnet 35 and a positioning stage 32 associated with a probe 38. An amount of a fluid 34 can be located on a substrate 36. During use, the positioning stages 30, 32 can be utilized to locate the magnet 35 and the probe 38 such that the two are within magnetic communication distance of one another. As shown in the series of images in FIG. 6, under the influence of the magnetic field, the probe 38 can move toward the fluid 34 and, upon contact, can absorb some or all of the fluid 34.

Commercially available microfluidic devices are typically monolithic stationary platforms with multiple channels to which the liquid is delivered either by a pipette or by a pump. The flexible probes described herein can broaden the applications and user-friendliness of microfluidic devices. The fiber-based flexible probe platform here developed opens up many opportunities for a plurality of applications such as probing and manipulating hazardous liquids, extracting biofluids from microorganisms or secretory glands, or operating on single cells.

Example

Probe Manufacturing

Two grams of PVDF (Goodfellow Corporation) and 0.2 grams of PEO (Mw=1,000 kDa, Sigma-Aldrich) were dissolved in 10 grams of dimethylacetamide (DMAc) (Spectrum) at 55° C. All chemicals were used as received without further purification. The prepared polymer solution was placed in a 10-mL syringe. A flexible syringe heater (Watlow, EHG SL10) was attached to the syringe to maintain the temperature at 55° C. The syringe with its heater was placed on the syringe pump (New Era Pump System, NE-300).

A rotating mandrel with four alumina bars separated from each other by 20 cm as illustrated in FIG. 2 was used as a fiber collector 18. A high-voltage power supply (Glassman High Voltage, Inc.) 16 was connected to the syringe through a stainless-steel needle 12 (Gauge 20, EXEL) and a 35-cm wide gap separated the needle end from the nearest face of the collector 18. The flow rate was controlled at 0.2 mL/hr. A positive voltage varying between 8-10 kV was applied to the needle 12 until a fiber jet and Taylor cone were produced. A second high-voltage power supply was attached to the collector 18 and a negative charge of 1 kV was applied. The device for fiber collection included two ¾-inch diameter circular wire brushes, mounted co-axially and each attached to a miniature DC motor as illustrated in FIG. 4. The same device was used to form yarns by spinning the brushes in the opposite directions. The number of revolutions and the rate of twisting was controlled with totalizer counters (Crouzet 2108) and optical reflection sensors (OPTEC Technology OPB704WZ) operating in the infrared range of light, thus avoiding any interference with other devices. Fibers were prepared at ambient temperature, 23-25° C. Solid non-porous fibers were obtained at 25-35% relative humidity while porous fibers were obtained at 65% relative humidity even without a separate PEO removal step.

Probe Characterization by Fourier Transform Infrared Spectroscopy (FT-IR)

Figure 7:
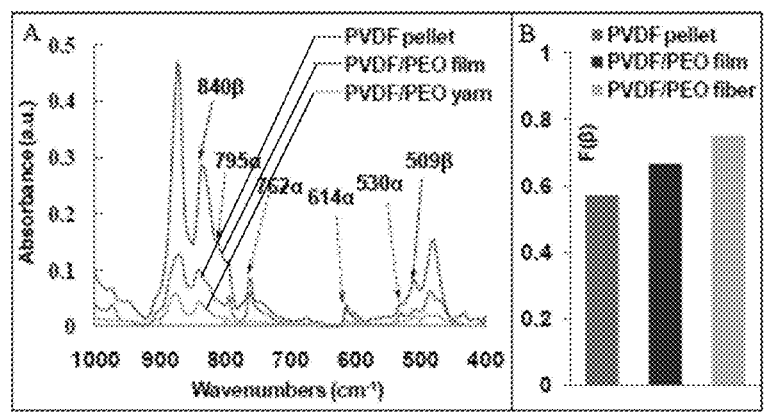
FIG. 7A shows IR spectra of PVDF pellets, PVDF/PEO films obtained by dip coating of glass slides, and electrospun PVDF/PEO fibers.
FIG. 7B illustrates the β/α ratios for PVDF pellets, PVDF-PEO film and electrospun PVDF-PEO fibers.

FT-IR spectra of the electrospun fibers were measured on Nicolet 550 Magna-IR spectrometer in the 400-1000 cm$^{-1}$ range of wave numbers. FIG. 7A shows three different IR spectra of PVDF pellets, PVDF/PEO films obtained by dip coating of glass slides, and electrospun PVDF/PEO fibers.

The $C_2H_2F_2$ molecular unit cells in the PVDF chain have net dipole moments, pointing from the electronegative fluorine to the hydrogen, and can crystallize forming different phases with different dipole orientations. It is known that the β-phase mostly consists of $CF_2$—$CH_2$ dipoles oriented in the same directions, i.e., this phase is ferroelectric. In the α-phase, the dipoles are counter-directed and form clusters with zero net moment, i.e., this phase are not ferroelectric. β- and α-phases can be distinguished by their spectral characteristics: absorption bands of the β-phase are situated at 509 and 840 cm$^{-1}$ and absorption bands of the α-phase appear at 530, 614, 762, and 795 cm$^{-1}$. In the electrospun PVDF/PEO fibers, the fraction of β-crystals appeared greater than that found in the PVDF pellets as shown in FIG. 7B. Quantitatively, about 30% increase of the β-crystals was observed in electrospun fibers. This analysis suggests that electrospinning favors the formation of the β-phase in the nanofibers. This analysis, however, did not provide any information about the direction of the polarization vector in the fibers. One can assume that the polarization vectors in crystallites are randomly oriented, because the external field changed frequently owing to the mandrel rotation as well as because of flipping of the field directions between each pair of charged arms.

Proboscis Characterization: Scanning Electron Microscope and Optical Microscope

Figure 8:
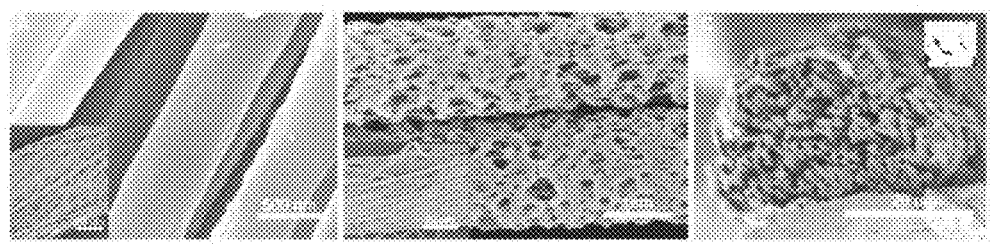
FIG. 8 shows SEM images of solid non-porous electrospun fibers (FIG. 8A), porous electrospun fibers (FIG. 8B) and a yarn formed of the porous fibers (FIG. 8C).

The morphological structure of the PVDF/PEO fiber surfaces and yarns was examined with a Hitachi Field Emission scanning electron microscope (FESEM-Hitachi 4800). FIG. 8A shows the typical morphology of solid PVDF fibers. FIG. 8B shows PVDF/PEO nanoporous fibers after dissolution of PEO in water, and FIG. 8C is a cross-section of yarn formed from the PVDF/PEO fibers. The black areas in the insert of FIG. 8C show the pores in an undisturbed spot after the yarn cutting. This area suggests that the porosity is close to 10%. The fiber diameters ranged between 0.8 and 1.8 μm, giving an average diameter of about 1.2 μm.

Optical microscopy (Olympus BX-51) was employed to examine the reproducibility of the probes. Several sets of PVDF/PEO yarns were electrospun under identical conditions as described above. The time of electrospinning and twist rate were varied. Measurements of yarn diameter were taken at 10 points along each yarn. FIG. 5 shows the diameters of eight different yarns averaged over 10 points each. As shown, the yarns have reproducible average diameters. The thicker the fiber band to start with, the easier it is to produce yarns with reproducible diameters. The thinnest reproducible yarns were 20 μm in diameter.

Fiber Porosity

Figure 9:
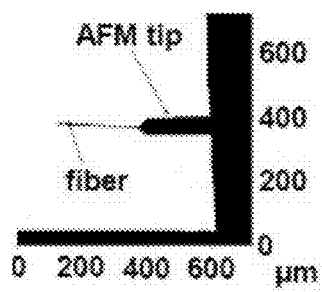
FIG. 9 illustrates a single fiber attached to an atomic force microscope (AFM) tip.

To determine the fiber porosity, a micro-sized piece of as-spun fiber was cut using the tip of an AFM (Dimension 3100 AFM, Veeco 50 Inc). Following, this piece was glued to an AFM tip for further analysis as shown in FIG. 9 (fiber porosity and elasticity measurements were carried out in collaboration with Dr. Igor Luzinov's group of Clemson University and published in Ref. Nanoscale, 3, 46854695 (2011)). The porosity measurement using AFM is premised on the fact that the resonance frequency of the AFM cantilever is very sensitive to minute changes in mass. The resonance frequency of the AFM cantilever will depend on the mass of absorbed liquid, i.e. on its volume. Hence the porosity, which is the ratio of the pore volume to the fiber volume, can be estimated directly. It was also confirmed that at time increments shorter than the time of droplet disappearance—which was about 20 minutes—the swelling of PVDF/PEO films was not significant, e.g., less than 5%. Therefore, swelling effect could be safely neglected and the experiments were interpreted based on physical flow phenomena.

Assuming that all pores are filled completely with the liquid, the fiber porosity was estimated as $$\varepsilon_f = \frac{V_{liquid}}{V_{liquid} + V_{matrix}} = \frac{1}{1 + V_{matrix}/V_{liquid}} = \frac{1}{1 + V_{matrix}\rho_{liquid}/M_{liquid}} \quad (1)$$

where $V_{liquid}$ is the volume of absorbed liquid, which is equal to the volume of pores and $V_{matrix}$ is the volume of polymer matrix calculated through the fiber mass, mass fractions (M) of the used polymers, and their densities (ρ) as $$V_{matrix} = V_{PEO} + V_{PVDF} \quad (2)$$

$$= \frac{M_{PEO}}{M_{PEO} + M_{PVDF}} \frac{M_{fiber}}{\rho_{PEO}} + \frac{M_{PVDF}}{M_{PEO} + M_{PVDF}} \frac{M_{fiber}}{\rho_{PVDF}}$$

To ensure complete filling of nanopores in the fiber, Galwick (Porous Materials, Inc) was chosen as the filler. Galwick has very low surface tension (σ=16 dynes/cm$^2$) and it wets PVDF and PEO surfaces completely. Using AFM, the tip with the attached fiber was immersed into a Galwick drop. Then, the new value of the resonance frequency was measured. Since the elastic constant of this complex spring is maintained, the change of the resonance frequency is mostly controlled by the added mass. $M_{Galwick}$ and $M_{fiber}$ were thus measured. Substituting in equations (1) and (2) the measured ratio $M_{Galwick}/M_{fiber}$ was found to be 5.12. Given the values $M_{PEO}/M_{PVDF}=0.1$, $\rho_{Galwick}=1.8212$ g/cm$^3$, $\rho_{PVDF}=1.76$ g/cm$^3$, and $\rho_{PEO}=1.13$ g/cm$^3$, it was estimated that the porosity of a single fiber was 0.82. This high porosity suggests that even a single fiber appears to be a good candidate for design of probes enabling one to collect and retain liquids in pores. When the fibers are twisted in the yarn, thus forming large micropores between them, the transport properties of the formed yarns can be significantly enhanced.

Analysis of Pore Size Distribution

Figure 10:
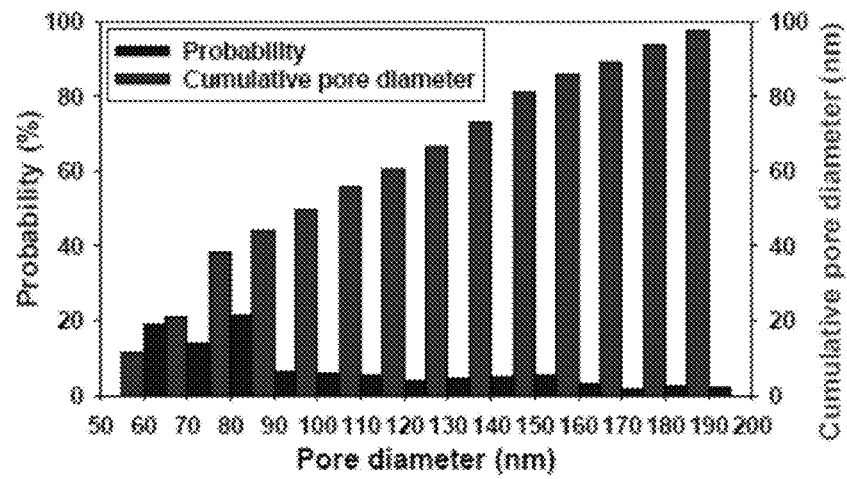
FIG. 10 illustrates the pore size distribution of electrospun nanoporous PVDF-PEO fibers.

The pore size distribution of the fibers was analyzed by using imageJ software (available from the National Institutes of Health). The images from FIG. 8B were cropped into several 2-μm×1-μm pieces and the number of pores in each picture was calculated. ImageJ also provided the pore area. To estimate the pore diameter, it was assumed that all pores were made of circular cylinders with diameter d. The results are provided in FIG. 10, which shows that most pores had diameters in the range of about 60 nm to about 80 nm. The average diameter was calculated as $$Dp = \Sigma f_i * d_i,$$

where f is the probability of finding the diameter $d_i$, and subscript i corresponds to the site at which the pore diameter was measured within the prescribed range from 50 to 190 nm. The average pore diameter was found to be about 98. The dark column shows on FIG. 10 shows the frequency of appearance of a fiber with a certain diameter, and the numbers above the lighter columns show the cumulative pore diameter, which approaches the average pore diameter of 98 nm.

Determination of Elastic Properties

Figure 11:
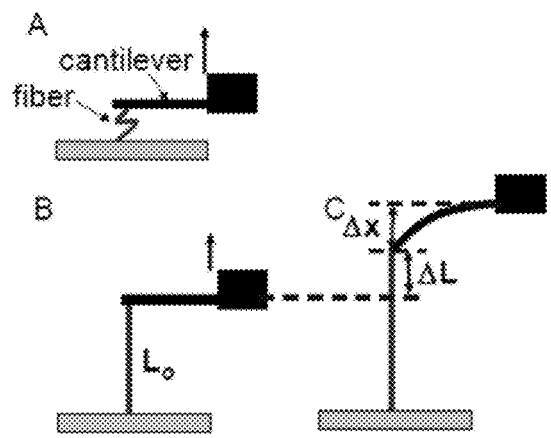
FIG. 11A-11C is a schematic illustration of an experimental protocol to study mechanical properties of single fibers by use of an AFM.

To experimentally evaluate the elasticity of a single PVDF/PEO fiber, an atomic force microscope (Dimension 3100 AFM, Veeco Inc) was used as illustrated in FIG. 11. A monolayer of the fiber web was electrospun onto a silicon wafer (SEH America Inc.). A drop of epoxy glue was placed on the wafer surface. A single fiber was located with the AFM and cut out by the AFM tip to the size of several hundred micrometers. Another end of the fiber was attached to the AFM cantilever by epoxy glue. Following these preparations, the AFM cantilever was moved up in 1 µm increments, while the voltage signal corresponding to the vertical deflection of the cantilever was monitored. After each successive increment, the fiber was released to attain a mechanical equilibrium.

The fibers typically reached equilibrium in less than 5 minutes, as was indicated by the constancy of the vertical deflection. During the first stages of incremental elevation of the cantilever, the deflection stayed at zero level after equilibration. This first—zero-force stage was associated with straightening of the fiber. This transition from a loose to a stretched state is shown schematically in FIG. 11A-11C. When the fiber was straightened, further elevation of the cantilever resulted in deflection of the cantilever tip. The cantilever tip was used as an indicator of fiber deformation; by measuring the tip deflection and knowing the force constant of the cantilever, the fiber stiffness was estimated.

As follows from the schematic in FIG. 11B and FIG. 11C, if $L_0$ is the fiber length before deformation, $\Delta x$ is the vertical deflection of the cantilever tip, and $\Delta L$ is the fiber elongation, then the incremental change of the cantilever position after n steps is $\Delta x + \Delta L = n\sigma$, where $\sigma$ is the incremental elevation of the cantilever; $\delta = 1$ µm in these experiments. Cantilever deflection was calculated from the voltage reading corresponding to the vertical deflection. Deflection sensitivity was determined prior to the experiment. Using measured $\Delta x$, $\Delta L$ was obtained at each step n. The force was calculated as $F = k\Delta x$, where k is the force constant of the AFM cantilever (NSC11, MikroMasch Inc). With the given force, the Young's modulus was estimated as $E = F*L_0/(\Delta L*S)$, where S is the fiber cross-sectional area before deformation. It is expected that the cross-sectional area will decrease upon deformation; therefore these moduli provide a lower estimate of the material's elasticity.

Figure 12:
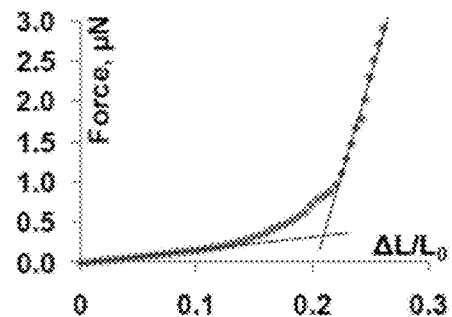
FIG. 12 presents the force-elongation curve of a PVDF-PEO fiber obtained by the protocol of FIG. 11A-11C.

The results are presented in FIG. 12. The force/elongation curve has two parts with distinct slopes. This behavior is a typical mechanical signature of a porous material. The first linear part of the curve corresponds to the initial fiber extension, when the pore walls buckle under a weak force. The corresponding modulus is very small, about 1.5 MPa, which is significantly lower than the elastic modulus of solid PVDF fibers and films, $E_f$ was determined to be about 3.5 GPa, confirming that the fiber was highly porous. The second asymptotic region of deformation is associated with the material densification and pore collapse, which results in the material hardening. In this extension regime, the Young's modulus was found to be two orders of magnitude greater, about 50 MPa.

By weakening the elastic properties of single fibers, one weakens the elastic properties of the whole yarn. For a quantitative evaluation of the reduction of the yarn elastic modulus, the bending modulus of the yarn was measured. The yarn was horizontally suspended and clamped from one end, while the other end was loaded with different weight. Tip deflection versus applied weight was analyzed using the Euler elastic equations. Assuming that all fibers in each yarn cross-section deform uniformly, one would expect that each single fiber in the bent yarn is subject to small strains corresponding to the first linear part of the force-elongation curve. While the modulus of a single fiber was about 1.5 MPa, it was found that the Young's modulus of the 80-150 µm diameter yarns varied between about 50 MPa and about 220 MPa, depending on the compaction density of fibers in the yarn. It is also expected that as the cross-sectional area of the fibers will decrease upon deformation, the moduli during use may be somewhat higher than these figures. In any case, however, the yarns formed from the disclosed fibers can be much more flexible than solid textile fibers and yarns, which typically have Young's moduli measured in the gigapascal range.

Determination of Wicking Properties

Figure 13:
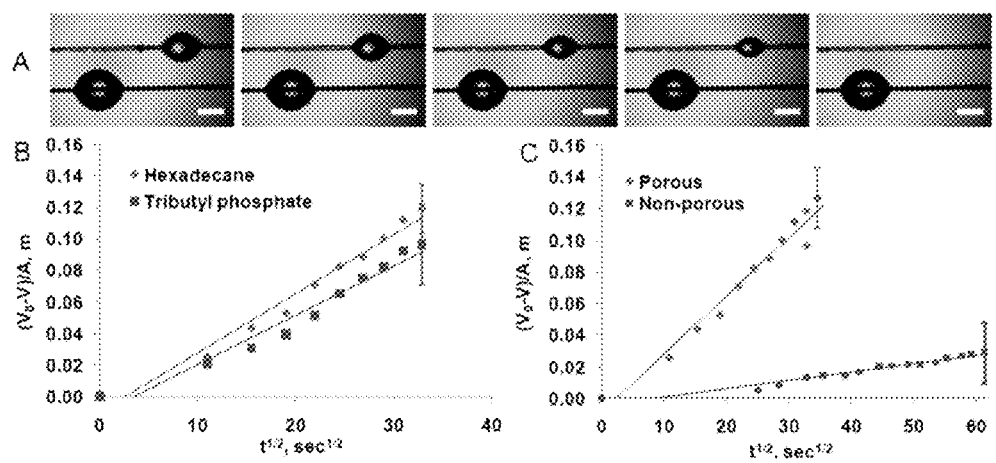
FIG. 13A presents a series of pictures illustrating the wicking kinetics of a hexadecane droplet (~4 microliters) into a PVDF/PEO yarn (upper) made of nanoporous fibers. An 80-μm copper wire (lower) with a hexadecane droplet was used as the reference.
FIG. 13B presents the comparative absorption kinetics of hexadecane and TBP droplets by yarns made of porous PVDF/PEO fibers.
FIG. 13C presents the comparative absorption kinetics of hexadecane droplets by yarns made of porous and non-porous fibers. The error bar corresponds to the highest standard deviation in the experiments.

In a first series of experiments it was confirmed that the wicking properties of the produced yarns were reproducible. Droplets of wetting nonvolatile liquids, hexadecane (HEX) and tributyl phosphate (TBP) were used for the evaluation of wicking properties of the yarns. These liquids were chosen as simulants of hazardous liquids. Droplets with initial volume $V_0$ were deposited on yarns, as shown in FIG. 13A. The drop volume V(t) was defined at each increment of time t by fitting the drop profile with Carrol's unduloid, an analytical solution of the Laplace equation of capillarity that describes the drop shape as a function of its volume. FIG. 13A shows a sequence of pictures of a hexadecane droplet during its absorption by the yarn (upper line of FIG. 13A). To confirm that the droplet did not evaporate during absorption experiments, but was absorbed by the yarn, a reference hexadecane droplet was placed on a copper wire (lower line of FIG. 13A). As clearly seen from FIG. 13A, this reference droplet did not change its volume appreciably, thus, proving that the yarn did take the drop in. The change of the droplet volume $(V_0 - V(t))$ as a function of time was filmed and analyzed. The arrows on FIG. 13A show that the drop penetrates into the yarn in both directions. The scale bar is 500 µm.

FIG. 13B shows the results of these absorption experiments conducted on four porous yarns. A is the yarn cross-section, $V_0$ is the initial drop volume, and V is the drop volume at time t. The absorption kinetics for both tested liquids followed the square-root-of-time law, also known as the Lucas-Washburn law. The slope fitting lines in FIG. 13B, or wicking constants, are close to each other, further suggesting that the yarn properties are very repeatable from one sample to another and that the given similarity is not just a chance event, but an expected consequence of the similarity of liquid properties as provided in Table 1, below.

TABLE 1

| Property at (20° C.-25° C.) | Tributyl phosphate (TBP) | n-Hexadecane (HEX) |
| --- | --- | --- |
| Color | Colorless | Colorless |
| Molecular formula | $C_{12}H_{27}O_4P$ | C16H34 |
| (Molecular Weight) | (Mw: 266.31) | (Mw: 226.238) |
| Viscosity (mPa · s) | 3.80 | 3.03 |
| Surface tension (mN/m) | 31.7 (measured: 29.94) | 27.47 (measured: 23.28) |
| Density (g/cm$^3$) | 0.97 | 0.773 |
| Vapor Pressure (mm Hg) | 2.6 × 10−6 @ 25° C. 27 @ 178° C. | 1 @ 105° C. |

In a second series of experiments, with three porous and three non-porous yarns, it was shown that the absorption properties of yarns made of solid non-porous fibers were very different from those of porous fibers. As demonstrated in FIG.

13C, the wicking constant of yarns made of solid nonporous fibers was significantly smaller.

Electric Field-Controlled Motion of a Probe

The performance of an artificial probe was demonstrated by absorbing droplets of tributyl phosphate (TBP), a popular simulant of hazardous liquids and a solvent for many hazardous chemicals. A schematic of the system used is shown in FIG. 14A and a series of images taken during the demonstration is shown in FIG. 14B.

Figure 14:
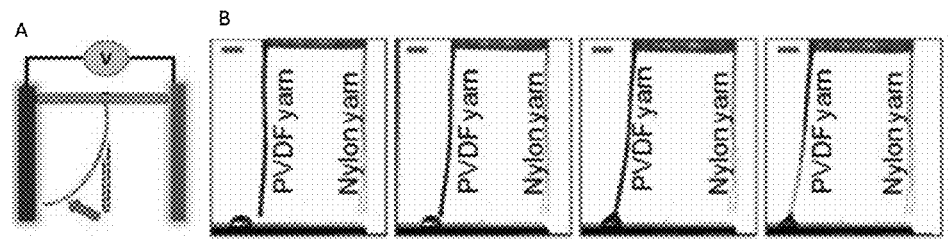
FIG. 14A presents a schematic of a method for manipulation of a probe with an electric field generated by two vertical electrodes.
FIG. 14B presents a series of images of a probe absorbing a liquid droplet by use of an electric field.

As shown in FIG. 14A, two copper plates were placed and fixed vertically and parallel to each other, forming an 18-mm gap in between. One plate was connected to a power supply (Glassman FC series) and the other plate was grounded.

FIG. 14B shows the use of the system of FIG. 14A. The solid black fiber on the left is a probe as described herein; the gray fiber on the right is a nylon yarn utilized as a control. The scale bar is 2 mm. The 320-μm diameter probe was vertically suspended between the two electrodes. The upper end of the probe was clamped to a holder and the lower end was free to move. A 0.34-μL TBP droplet was deposited onto the substrate at the bottom of the cell. This cell was enclosed with a transparent 60×30×18 mm box, thus preventing any perturbations of the probed caused by air flow. After application of an 8-kV potential, probe flexion was observed and the free end moved toward the droplet. In this field, no appreciable change of the droplet shape was observed. The process was filmed with a video camera (Dalsa Falcon 1.4, Canada). When the probe touched the droplet, the power was turned off. Following, the tip of the probe was held attached to the droplet by only the surface tension of the liquid. Finally, when the droplet was completely wicked into the yarn, the yarn bent back to its initial straight shape.

A nylon yarn suspended in the cell as a reference stayed straight during the entire experiment (FIG. 14B). The nylon reference yarn had the same diameter and length as its experimental counterpart. This evidence favors the hypothesis that the PVDF/PEO fibers contain a substantial amount of ferroelectric crystals.

Example 2

Electrospun fibers were formed as described in Example 1 from various materials. Polymers included Poly(ethylene oxide) (PEO), cellulose acetate (CA), poly(methyl methacrylate) (PMMA), polyacrylonitrile (PAN), polyvinyl alcohol (PVA), and polyvinylidene fluoride (PVDF). Electrospinning solution information is provided in the table, below:

| Polymer solution | Solvent | Concentration (wt %) |
|---|---|---|
| CA/PEO | Dimethylacetamide | 8~17 wt % |
| CA/PMMA | Dimethylacetamide | 12~16 wt % |
| PAN/PMMA | Dimethylacetamide | 10~17 wt % |
| PAN/CA | Dimethylacetamide | 10~17 wt % |
| PVDF/PEO | Dimethylacetamide | 12~18 wt % |
| PAN | Dimethylacetamide | 8~15 wt % |
| PMMA | Methyl Ethyl Ketone | 10~16 wt % |
| PEO | Water | 2~5 wt % |
| PVA | Water | 10~16 wt % |

Example 3

Yarns were formed of electrospun fibers as described in Example 1, above. Following formation, the permeability of the yarns was determined. Formation materials, yarn twist characteristics, and permeability is presented in the table below.

| Polymer solution | Solvent | Turns per centimeter (tpc) | Permeability ($m^2$) |
|---|---|---|---|
| CA/PMMA/PEO | Dimethylacetamide | 12 | $4.2 \pm 0.6E-12$ |
| CA/PMMA | Dimethylacetamide | 12 | $4.6 \pm 0.5E-13$ |
| PVDF/PEO | Dimethylacetamide | 12 | $1.3 \pm 0.1E-13$ |
| PAN | Dimethylacetamide | 12 | $8.8 \pm 0.3E-14$ |

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A fluidic probe comprising a plurality of oriented fibers, individual fibers of the plurality of oriented fibers including nano-sized pores in the fiber bodies, the fluidic probe including the plurality of oriented fibers twisted together, wherein the twisted plurality of fibers defines micro-sized pores between the individual twisted fibers, the fluidic probe exhibiting fluid absorption via the nano-sized pores and the micro-sized pores.

2. The fluidic probe of claim 1, wherein the nano-sized pores have an average cross-sectional diameter of less than about 200 nanometers.

3. The fluidic probe of claim 1, wherein the micro-sized pores have an average cross-sectional diameter of less than about 10 micrometers.

4. The fluidic probe of claim 1, wherein the fibers are electrospun fibers.

5. The fluidic probe of claim 1, wherein the fibers comprise an electroactive polymer.

6. The fluidic probe of claim 1, wherein the fibers comprise polyvinylidene fluoride.

7. The fluidic probe of claim 1, wherein the fibers comprise a polymeric blend.

8. The fluidic probe of claim 1, wherein the fibers further comprise nano-sized particles.

9. The fluidic probe of claim 8, wherein the particles comprise superparamagnetic particles.

10. The fluidic probe of claim 1, wherein the probe further comprises one or more materials that exhibits an optically detectable response in the presence of a particular compound.

* * * * *